United States Patent [19]

Metzner

[11] Patent Number: 4,546,203

[45] Date of Patent: Oct. 8, 1985

[54] FACILE SYNTHESIS OF β-HYDROXY-β-METHYLGLUTARIC ACID

[75] Inventor: Ernest K. Metzner, Del Mar, Calif.

[73] Assignee: American Hoechst Corporation, Somerville, N.J.

[21] Appl. No.: 588,263

[22] Filed: Mar. 12, 1984

Related U.S. Application Data

[63] Continuation of Ser. No. 329,654, Dec. 11, 1981, abandoned.

[51] Int. Cl.[4] .................. C07C 51/235; C07C 59/245
[52] U.S. Cl. .................................. 562/538; 562/539; 562/582

[58] Field of Search ...................... 562/582, 538, 539

[56] References Cited

FOREIGN PATENT DOCUMENTS

| | | | |
|---|---|---|---|
| 709668 | 7/1941 | Fed. Rep. of Germany | 562/538 |
| 2853394 | 12/1978 | Fed. Rep. of Germany | 562/538 |
| 1068650 | 5/1967 | United Kingdom | 562/538 |

Primary Examiner—Paul J. Killos
Attorney, Agent, or Firm—J. Cartiglia; N. Jensen

[57] ABSTRACT

β-Hydroxy-β-methylglutaric acid is prepared by treating 3-methyl-1,3,5-pentanetriol in aqueous media with a permanganate salt.

8 Claims, No Drawings

FACILE SYNTHESIS OF β-HYDROXY-β-METHYLGLUTARIC ACID

This is a continuation of application Ser. No. 329,654 filed Dec. 11, 1981 now abandoned.

BACKGROUND OF INVENTION

β-Hydroxy-β-methylglutaric acid (HMG) is well established as a hypolipidemic and hypocholesterolemic agent (Yusufi et al, Atherosclerosis,20, 517(1974) and U.S. Pat. No. 3,629,449).

The synthesis of this biologically important compound has been primarily accomplished by (1) oxidation of diallylmethyl carbinol or 3-hydroxy-3-methyl-hex-5-enoic acid with ozone and hydrogen peroxide (Klosterman et al, J. Am. Chem. Soc. 76, 1229(1954); Biochemical Preparations, 6, 25(1958); Tschesche et al, Ann. der Chemis, 631, 61(1960) and (2) a Reformatsky reaction between ethyl acetoacetate and ethyl bromoacetate (Adams et al, J. Am. Chem. Soc. 75, 2377(1953).

Both of the above described synthetic methods for the preparation of HMG embrace difficult multi-step procedures, require complicated purification schemes and produce low yields.

The present invention overcomes the disadvantages of the prior art by providing a simple one step synthesis of HMG from a readily available starting material. Use of the procedure described herein permits large scale synthesis of the HMG at very low cost.

SUMMARY OF THE INVENTION

The present invention relates to an improved process for the production of β-hydroxy-β-methylglutaric acid (HMG). More particularly, the present invention relates to a process for preparing HMG which comprises treating 3-methyl-1,3,5-pentanetriol in aqueous media with a permanganate salt selected from the group consisting of potassium permanganate and sodium permanganate and recovering β-hydroxy-β-methyl glutaric acid from the aqueous media.

DETAILED DESCRIPTION OF THE INVENTION

In accordance with the present invention, β-hydroxy-β-methylglutaric acid (HMG) is prepared by treating 3-methyl-1,3,5-pentanetriol with a permanganate salt selected from the group consisting of sodium permanganate and potassium permanganate.

The reaction is carried out in aqueous media which is preferably neutral or alkaline. The use of an acidic medium is a disadvantage because the yield of HMG is lower and the product is somewhat more difficult to isolate. Strongly acidic reaction conditions should be avoided due to the susceptibility of HMG to dehydration.

The reaction temperature employed herein can range from about 10° C. to 110° C. with a temperature range of 30° C. to 45° C. being preferred. A reaction time of approximately three hours is satisfactory, but the reaction time can vary from 10 minutes to several days depending on the scale of the reaction. The mole ratio of permanganate to triol can range from 3:1 to 5:1 with a ratio of 4:1 being preferred.

The reaction product is recovered by conventional means. For example, insoluble manganese dioxide is removed from the reaction mixture by filtration or centrifugation. The filtrate or centrifugate containing the product is then acidified to a pH of 1-2 with concentrated HCl. The resulting acidified filtrate or centrifugate is then concentrated to yield the acid residue which is further purified by recrystallization from a suitable solvent, such as ethyl acetate or acetonitrile.

The yields of HMG produced by the process of the present invention are excellent, i.e. yields in excess of 50% are routinely obtained.

The term "aqueous media" as used herein preferably refers to water, however minor amounts of water miscible solvents that do not interfere with the oxidation reaction may be used in combination with water.

3-methyl-1,3,5-pentanetriol utilized herein was obtained from Kuraray Isoprene Chemical Co., Ltd., Tokyo, Japan.

DESCRIPTION OF SPECIFIC EMBODIMENTS

The following specific description is given to enable those skilled in the art to more clearly understand and practice the present invention. It should not be considered as a limitation upon the scope of the invention but merely as being illustrative and representative thereof.

EXAMPLE

A 2 liter reaction vessel is charged with 800 ml of water, 240 g potassium permanganate (1.52 mole) and 3 ml 19N sodium hydroxide. The resulting reaction mixture is stirred for approximately 10 minutes to dissolve most of the permanganate and the temperature is adjusted to approximately 25° C. While the resulting solution is further agitated at room temperature, 50 ml of a solution of 54 g of 3-methyl-1,3,5-pentanetriol (0.4 mole) in 150 ml of water is added. After the addition of 50 ml of the triol solution the temperature will rise to about 35° C. After approximately 10 minutes, the remaining triol solution is added dropwise over a period of 15 minutes. During the addition, the temperature is maintained at 40° to 43° C. by cooling the reaction vessel in an ice bath.

After all of the triol solution has been added, the reaction will continue to exotherm for about one hour. During this time, and thereafter for a period of 3 hours, the temperature is maintained at 43° C. Thereafter, the reaction mixture is heated to 80° C. for approximately 10 minutes and then allowed to cool to room temperature.

The reaction mixture is filtered and the filter cake is suspended in 200 ml of water. The suspension is stirred well and then filtered. The filtrates are combined and acidified to pH 1.5 with concentrated hydrochloric acid. The acidified filtrate is then dried under reduced pressure at 60° to 65° C. to obtain a dry salt cake.

The above-obtained salt cake is extracted with approximately 200 ml of acetone with the salt being removed from by filtration. Thereafter, the cake is extracted again with two 50 ml portions of acetone.

The acetone extracts are combined and dried under reduced pressure to obtain a stiff syrup which is dissolved in approximately 100 ml of boiling acetonitrile. Four grams of anhydrous magnesium sulfate and 1 gram of activated carbon are added to the hot solution which is then filtered. The resulting product is allowed to crystallize with stirring at room temperature for 3 hours. The resulting slurry is stirred with cooling to 0° C. The crystallized product is recovered by filtration, washed with ethyl acetate cooled to −20° C. and dried under reduced pressure at 45° C. to yield 26–28 grams of β-hydroxy-β-methylglutaric acid, m.p. 105° C.–108° C.

What is claimed is:

1. A process for preparing β-hydroxy-β-methylglutaric acid which comprises oxidizing 3-methyl-1,3,5-pentanetriol in aqueous media with a permanganate salt.

2. A process according to claim 1 wherein said permanganate salt is selected from the group consisting of potassium permanganate and sodium permanganate.

3. A process for preparing β-hydroxy-β-methylglutaric acid which comprises oxidizing 3-methyl-1,3,5-pentanetriol in aqueous media with a permanganate salt selected from the group consisting of potassium permanganate and sodium permanganate.

4. A process according to claim 1 further comprising recovering β-hydroxy-β-methylglutaric acid from said aqueous media.

5. A process according to claim 1 wherein said oxidizing is carried out at a temperature of from about 10° C. to 110° C.

6. A process according to claim 5 wherein said temperature is from about 30° C. to 45° C.

7. A process according to claim 3 wherein the molar ratio of permanganate salt to 3-methyl-1,3,5-pentanetriol is in the range of 3:1 to 5:1.

8. A process according to claim 3 wherein said aqueous media is neutral or alkaline.

* * * * *